United States Patent [19]

Sasse et al.

[11] Patent Number: 4,865,641
[45] Date of Patent: Sep. 12, 1989

[54] HERBICIDAL NEW THIAZOLYL ETHER AND THIOETHER DERIVATIVES

[75] Inventors: Klaus Sasse, Bergisch-Gladbach; Reiner Fischer, Monheim; Hermann Hagemann, Leverkusen; Andreas Krebs, Odenthal; Michael Schwamborn, Cologne; Hans-Joachim Santel, Leverkusen; Robert R. Schmidt, Bergisch-Gladbach; Robert H. Strang, Duesseldorf, all of Fed. Rep. of Germany

[73] Assignee: Bayer Aktiengesellschaft, Leverkusen, Fed. Rep. of Germany

[21] Appl. No.: 166,137

[22] Filed: Mar. 9, 1988

[30] Foreign Application Priority Data

Mar. 13, 1987 [DE] Fed. Rep. of Germany ....... 3708201

[51] Int. Cl.⁴ .................... C07D 277/34; A01N 43/78
[52] U.S. Cl. ........................................ 71/90; 548/186; 548/187
[58] Field of Search ..................... 548/186, 187; 71/90

[56] References Cited

FOREIGN PATENT DOCUMENTS 639963 12/1983 Switzerland ........................ 548/186
1316574 5/1973 United Kingdom ................ 548/186

OTHER PUBLICATIONS

T. Jojima et al, Agr. Biol. Chem. 30, (9), p. 896 et seq. (1966).
Chemical Abstracts vol. 70.

Primary Examiner—Robert Gerstl
Attorney, Agent, or Firm—Sprung Horn Kramer & Woods

[57] ABSTRACT

Herbicidally active compounds of the formula

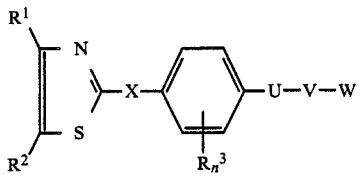

in which
$R^1$ represents hydrogen or alkyl,
$R^2$ represents hydrogen or alkyl,
with the proviso that $R^1$ and $R^2$ do not simultaneously represent hydrogen,
X represents oxygen or sulphur,
$R^3$ represents hydrogen, halogen, nitro, amino, cyano, alkyl, halogenoalkyl, alkoxy or halogenoalkoxy,
wherein the radicals $R^3$ can be identical or different,
n represents a number from 1-4,
U represents oxygen or sulphur,
V represents a

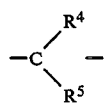

group,
$R^4$ and $R^5$ independently of one another represent hydrogen, alkyl, alkoxyalkyl or halogenoalkyl,
W represents a radical

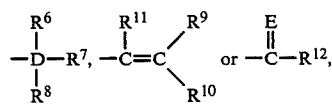

D represents carbon or silicon,
E represents oxygen or sulphur, and
$R^6$ through $R^{12}$ can have various meanings.
The starting materials wherein -U-V-W together are OH are also new.

10 Claims, No Drawings

HERBICIDAL NEW THIAZOLYL ETHER AND THIOETHER DERIVATIVES

The present invention relates to new substituted thiazolyloxy (or thio)aryl derivatives, processes for their preparation and their use as herbicides.

It is already known that certain carboxylic acid anilides or benzoic acid derivatives possess herbicidal properties (see R. Wegler "Chemie der Pflanzenschutz und Schädlingsbekämpfungsmittel" (Chemistry of Plant Protection and Pest-Combating Agents") Volume 2, pages 311–314 or 289–295; Volume 5 pages 200–217, Springer Verlag, Berlin 1970/1977, German Pat. No. 3,422,007). However, their action under certain conditions, for example at low rates of application, is not always satisfactory. Similarly, the selectivity in many cases leaves something to be desired.

It is also known that certain alkyl heterooxyaryl derivatives possess herbicidal properties (see T. Jojima et al. Agr. Biol. Chem. 30, (9) 896 et seq. (1966) or JA-OS (Japanese Published Specification) 9474/1967).

The herbicidal potency of these substances is however not always sufficient under practical conditions.

New thiazolyl derivatives of the general formula (I)

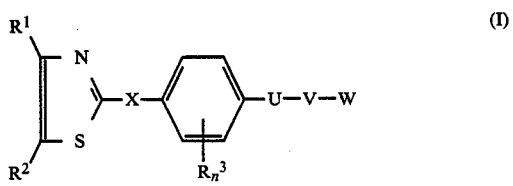

in which
$R^1$ represents hydrogen or alkyl,
$R^2$ represents hydrogen or alkyl,
with the proviso that $R^1$ and $R^2$ do not simultaneously represent hydrogen,
X represents oxygen or sulphur,
$R^3$ represents hydrogen, halogen, nitro, amino, cyano, alkyl, halogenoalkyl, alkoxy or halogenoalkoxy,
wherein the radicals $R^3$ can be identical or different,
n represents a number from 1–4,
U represents oxygen or sulphur,
V represents a

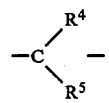

group,
$R^4$ and $R^5$ independently of one another represent hydrogen, alkyl, alkoxyalkyl or halogenoalkyl,
W represents a radical

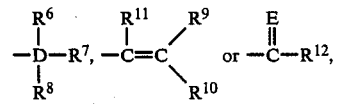

D represents carbon or silicon,
E represents oxygen or sulphur,
$R^6$, $R^{11}$ and $R^{12}$ independently of one another represent hydrogen, halogen, alkyl or halogenoalkyl, $R^7$ represents hydrogen, halogen, or alkyl which is optionally substituted by halogen; alkoxy, alkoxyalkyl or alkylthio,
$R^8$ represents halogen, a saturated or unsaturated aliphatic radical with 1 to 6 carbon atoms which is optionally substituted by halogen, alkoxy, alkoxyalkyl, alkylthio, formyl, alkylcarbonyl, alkoxycarbonyl, open-chain or cyclic acetal, open-chain or cyclic thioacetal, or
$R^7$ and $R^8$, together with the carbon atom to which they are bonded, form a 3- to 8-membered ring, which, apart from carbon, can also contain oxygen and/or sulphur and/or nitrogen as ring members and which can optionally be substituted by halogen, alkyl, alkoxy or alkoxyalkyl and which can contain one or more double bonds, or
$R^6$, $R^7$ and $R^8$, together with the carbon atom to which they are bonded, represent a radical of the structure

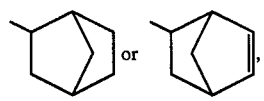

and
$R^9$ and $R^{10}$ independently of one another represent hydrogen, halogen, alkyl or halogenoalkyl,
have now been found.

If compounds of the general formula (I) contain an asymmetric carbon atom, then they can also exist in different enantiomeric forms. The invention relates both to the possible individual isomers and also to mixtures of the isomers.

One asymmetric centre is present when V represents the

group and $R^4$ and $R^5$ have different meanings, in which the asymmetric C atom, identified by *, can exhibit the R, S or R/S (racemate) configuration.

The second asymmetric center is present when W represents

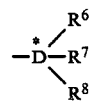

and D represents carbon and $R^6$, $R^7$ and $R^8$ have different meanings, in which the second asymmetric C atom can also exhibit the R, S or R/S (racemate) configuration.

It has furthermore been found that the 2-thiazolyl ether and thioether derivatives of the general formula (I) are obtained when
(A) compounds of the general formula (II)

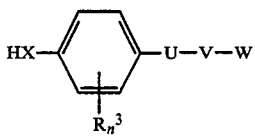

in which X, R³, U, V, W and n have the meanings given above, are reacted with compounds of the general formula (III)

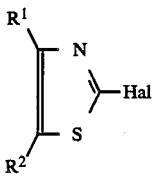

in which
R¹ and R² have the meanings given above and
Hal represents halogen,
in the presence of a diluent and if appropriate in the presence of an acid-binding agent, or when
(B) compounds of the general formula (IV)

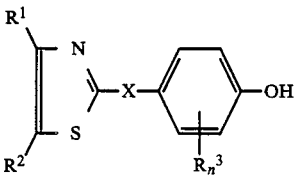

in which R¹, R², X, R³ and n have the meanings given above, are reacted with compounds of the general formula (V)

L—V—W      (V)

in which
V and W have the meanings given above and
L represents halogen, alkylsulphonyloxy with in each case 1 to 4 carbon atoms, halogenoalkylsulphonyloxy with in each case 1 to 4 carbon atoms or phenylsulphonyloxy or substituted phenylsulphonyloxy,
in the presence of a diluent and if appropriate in the presence of an acid-binding agent.

Finally, it has been found that the new 2-thiazolyl ethers and thioethers of the general formula (I) are characterized by very good herbicidal activity.

Surprisingly, the 2-thiazolyl ethers and thioethers of the general formula (I) according to the invention possess substantially better herbicidal properties than structurally similar known substances.

The carbon chains in the definitions can be straight or branched; halogen in each case represents fluorine, chlorine, bromine or iodine.

A general definition of the thiazolyl ethers and thioethers according to the invention is given by the general formula (I). Those compounds of the general formula (I) are preferred in which
$R^1$ represents hydrogen or $C_1$-$C_4$-alkyl,
$R^2$ represents hydrogen or $C_1$-$C_4$-alkyl,
with the proviso that $R^1$ and $R^2$ do not simultaneously represent hydrogen, X represents oxygen or sulphur,
$R^3$ represents hydrogen, halogen, $C_1$-$C_4$-alkyl, $C_1$-$C_4$-halogenoalkyl, $C_1$-$C_4$-alkoxy or halogeno-$C_1$-$C_4$-alkoxy, wherein the radicals $R^3$ can be identical or different,
n represents a number from 1–4,
U represents oxygen or sulphur,
V represents a

group,
$R^4$ and $R^5$ independently of one another in each case represent hydrogen, $C_1$-$C_4$-alkyl, $C_1$-$C_4$-alkoxy-$C_1$-$C_4$-alkyl or halogeno-$C_1$-$C_4$-alkyl,
W represents a radical

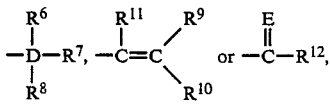

D represents carbon or silicon,
E represents oxygen or sulphur,
$R^6$, $R^{11}$ and $R^{12}$ independently of one another represent hydrogen, halogen, $C_1$-$C_6$-alkyl or halogeno-$C_1$-$C_6$-alkyl,
$R^7$ represents hydrogen, halogen, $C_1$-$C_6$-alkyl, $C_1$-$C_6$-alkoxy, $C_1$-$C_6$-alkoxy-$C_1$-$C_6$-alkyl, $C_1$-$C_6$-alkylthio or halogeno-$C_1$-$C_6$-alkyl, $R^8$ represents halogen, $C_1$-$C_6$-alkyl, $C_1$-$C_6$-alkoxy, $C_1$-$C_6$-alkoxy-$C_1$-$C_6$-alkyl, $C_1$-$C_6$-alkylthio, formyl, $C_1$-$C_6$-alkylcarbonyl, $C_1$-$C_6$-alkoxycarbonyl, $C_2$-$C_6$-alkenyl, $C_2$-$C_6$-alkinyl, halogeno-$C_1$-$C_6$-alkyl, halogeno-$C_2$-$C_6$-alkenyl, open-chain ketal, cyclic ketal with 5 or 6 ring members, open-chain acetal, cyclic acetal with 5 or 6 ring members, open-chain thioacetal or cyclic thioacetal with 5 or 6 ring members or
$R^7$ and $R^8$, together with the carbon atom to which they are bonded, form a 5- or 6-membered ring which, apart from carbon, can also contain 1 or 2 oxygen and/or sulphur and/or nitrogen atoms as ring members and which can be substituted by fluorine, chlorine, bromine and iodine, $C_1$-$C_4$-alkyl, $C_1$-$C_4$-alkoxy and/or $C_1$-$C_4$-alkoxy-$C_1$-$C_4$-alkyl and which can contain one or two double bonds or
$R^6$, $R^7$ and $R^8$, together with the carbon atom to which they are bonded, represent a radical of the structure

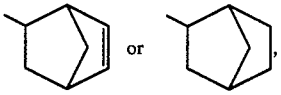

$R^9$ and $R^{10}$ independently of one another represent hydrogen, halogen, $C_1$-$C_6$-alkyl or halogeno-$C_1$-$C_6$-alkyl.

The optically active compounds of the general formula (I) are also preferred.

Those compounds of the general formula (I) are particularly preferred in which
$R^1$ represents hydrogen, methyl or ethyl,
$R^2$ represents hydrogen, methyl or ethyl, with the proviso that $R^1$ and $R^2$ do not simultaneously represent hydrogen, X represents oxygen or sulphur, $R^3$ represents hydrogen, halogen, methyl, ethyl, methoxy, ethoxy, halogeno-$C_1$–$C_2$-alkyl or halogeno-$C_1$–$C_2$-alkoxy, wherein the radicals $R^3$ can be identical or different, n represents a number from 1–4, U represents oxygen or sulphur, V represents a

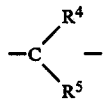

group, $R^4$ and $R^5$ independently of one another in each case represent hydrogen, methyl, ethyl, methoxymethyl, methoxyethyl, ethoxymethyl, ethoxyethyl or halogeno-$C_1$–$C_2$-alkyl, W represents a radical

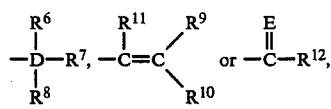

D represents carbon or silicon,

E represents oxygen or sulphur, $R^6$, $R^{11}$ and $R^{12}$ independently of one another represent hydrogen, fluorine, chlorine, bromine, iodine, $C_1$–$C_4$-alkyl or halogeno-$C_1$–$C_4$-alkyl, $R^7$ represents hydrogen, fluorine, chlorine, bromine, iodine, $C_1$–$C_4$-alkyl, $C_1$–$C_4$-alkoxy, $C_1$–$C_4$-alkoxy-$C_1$–$C_4$-alkyl, $C_1$–$C_4$-alkylthio or halogeno-$C_1$–$C_4$-alkyl, $R^8$ represents fluorine, chlorine, bromine, iodine, $C_1$–$C_4$-alkyl, $C_1$–$C_4$-alkoxy, $C_1$–$C_4$-alkoxy-$C_1$–$C_4$-alkyl, $C_1$–$C_4$-alkylthio, formyl, $C_1$–$C_4$-alkylcarbonyl, $C_1$–$C_4$-alkoxycarbonyl, $C_2$–$C_4$-alkenyl, $C_2$–$C_4$-alkinyl, halogeno-$C_1$–$C_4$-alkyl, halogeno-$C_2$–$C_4$-alkenyl, open-chain acetal, cyclic acetal with 5 or 6 ring members, open-chain thioacetal or cyclic thioacetal with 5 or 6 ring members, or $R^7$ and $R^8$, together with the carbon atom to which they are bonded, form a 5- or 6-membered ring which apart from carbon, can also contain 1 or 2 oxygen and/or sulphur and/or nitrogen atoms as ring members and which can be substituted by fluorine, chlorine, bromine and iodine, methyl, ethyl, methoxy, ethoxy, methoxymethyl, methoxyethyl, ethoxymethyl or ethoxyethyl and which can contain one or two double bonds, or $R^6$, $R^7$ and $R^8$, together with the carbon atom to which they are bonded, represent a radical of the structure

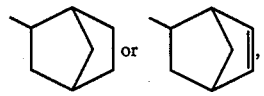

and $R^9$ and $R^{10}$ independently of one another represent hydrogen, halogen, $C_1$–$C_2$-alkyl or halogeno-$C_1$–$C_2$-alkyl.

The optically active compounds of the general formula (I) are particularly preferred.

Those compounds of the general formula (I) are very particularly preferred in which $R^1$ represents hydrogen, methyl or ethyl, $R^2$ represents hydrogen, methyl or ethyl, with the proviso that $R^1$ and $R^2$ do not simultaneously represent hydrogen, X represents oxygen or sulphur, $R^3$ represents hydrogen, fluorine, chlorine, bromine, methyl, ethyl, methoxy, ethoxy, trifluoromethyl or trifluoromethoxy, wherein the radicals $R^3$ can be identical or different, n represents a number from 1–4, U represents oxygen or sulphur, V represents a

group, $R^4$ and $R^5$ independently of one another in each case represent hydrogen, methyl, ethyl, methoxymethyl, methoxyethyl, ethoxymethyl, ethoxyethyl or halogeno-$C_1$–$C_2$-alkyl, W represents a radical

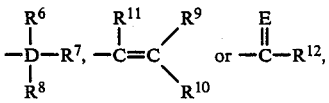

D represents carbon or silicon,

E represents oxygen or sulphur, $R^6$, $R^{11}$ and $R^{12}$ independently of one another represent hydrogen, fluorine, chlorine, methyl, ethyl, n-propyl, iso-propyl, n-, iso-, sec.- or tert.-butyl or halogeno-$C_1$–$C_2$-alkyl, $R^7$ represents hydrogen, fluorine, chlorine, methyl, ethyl, n-propyl, iso-propyl, n-, iso- or sec.-butyl, n-, iso- or sec.-butoxy, methoxymethyl, methoxyethyl, methoxy-n-propyl, methoxy-iso-propyl, ethoxymethyl, ethoxyethyl, ethoxy-n-propyl, ethoxy-iso-propyl, n-propoxymethyl, n-propoxyethyl, n-propoxy-n-propyl, n-propoxy-iso-propyl, methylthio, ethylthio, isopropylthio or halogeno-$C_1$–$C_2$-alkyl, $R^8$ represents fluorine, chlorine, $C_1$–$C_4$-alkyl, $C_1$–$C_4$-alkoxy, $C_1$–$C_4$-alkoxy-$C_1$–$C_4$-alkyl, $C_1$–$C_4$-alkylthio, $C_1$–$C_4$-alkylcarbonyl, $C_1$–$C_4$-alkoxycarbonyl, formyl, $C_2$–$C_4$-alkenyl, $C_2$–$C_4$-alkinyl, halogeno-$C_1$–$C_4$-alkyl, halogeno-$C_2$–$C_4$-alkenyl, halogeno-$C_2$–$C_4$-alkinyl, open-chain acetal, cyclic acetal with 5 or 6 ring members, open-chain thioacetal or cyclic thioacetal with 5 or 6 ring members or open-chain ketal or cyclic ketal with 5 or 6 ring members, or $R^7$ and $R^8$, together with the carbon atom to which they are bonded, form a 5- or 6-membered ring which, apart from carbon, can also contain oxygen and/or sulphur and/or nitrogen as ring members and which can be substituted by fluorine, chlorine, methyl, ethyl, methoxy, ethoxy, methoxymethyl, ethoxymethyl or ethoxyethyl and which can contain one or two double bonds, or $R^6$, $R^7$ and $R^8$, together with the carbon atom to which they are bonded, represent a radical of the structure

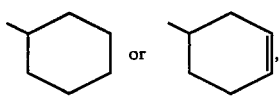

and $R^9$ and $R^{10}$ independently of one another represent hydrogen, halogen, $C_1$-$C_2$-alkyl or halogeno-$C_1$-$C_2$-alkyl.

The optically active compounds of the general formula (I) are also very particularly preferred.

If, for example, 4,5-dimethyl-2-chlorothiazole and 4-neopentyloxy-thiophenol are used as starting substances, then the course of the reaction of the process (A) according to the invention can be represented by the following scheme:

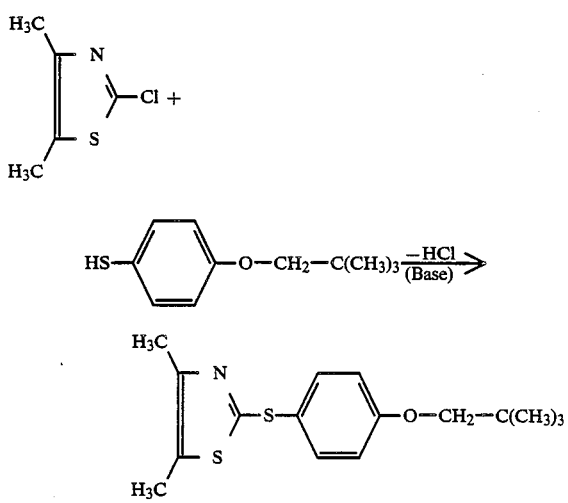

If, for example, 4-(4,5-dimethyl-2-thiazolylthio)-phenol and isobutyl tosylate are used as starting substances, then the course of the reaction of the process (B) according to the invention can be represented by the following scheme:

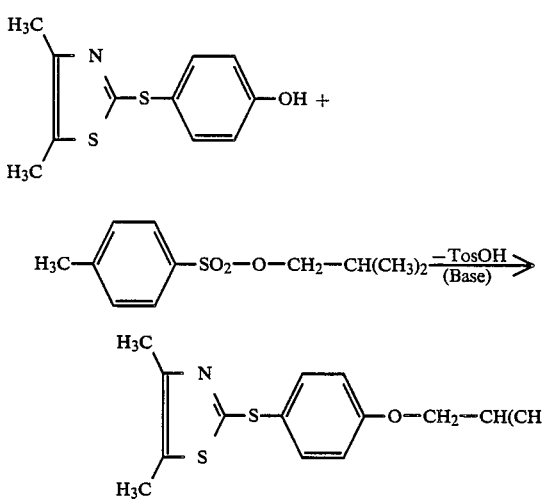

A general definition of the (thio)phenol derivatives required as starting substances for carrying out the process (A) according to the invention is given by the formula (II). In this general formula (II), X, $R^3$, U, V, W and n preferably have those meanings which have already been mentioned as preferred for these substituents in the description of the substances of the formula (I) according to the invention.

The thiophenol derivatives of the general formula (II) are in some cases known or can be synthesized in a simple manner by known methods (see, for example, Coll. Czech. Chem. Commun., 29, 2161 (1964), and some are the subject of an older application for patent protection submitted by this company.

The thiophenol derivatives of the general formula (II) in which X represents sulphur are obtained when (a) amino-(thio)phenol derivatives of the general formula (VII)

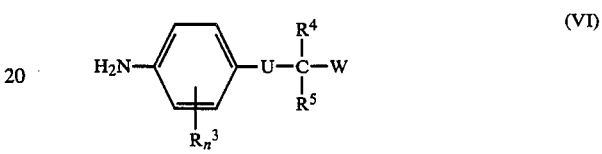

in which $R^3$, $R^4$, $R^5$, U, W and n have the meanings given above, are diazotized in a 1st step with a nitrating agent, if appropriate in the presence of a diluent and if appropriate in the presence of a reaction auxiliary, the diazotization product is reacted in a 2nd step in the presence of a diluent and in the presence of a base with alkali metal xanthate, and then the reaction product is heated in a 3rd step with alkali metal hydroxide in the presence of a diluent, or when (b) benzenesulphonyl chlorides of the general formula (VII)

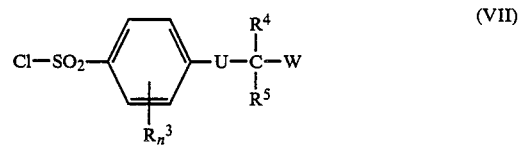

in which $R^3$, $R^4$, $R^5$, U, W and n have the meanings given above, are reduced with reducing agents, if appropriate in the presence of a diluent and if appropriate in the presence of a reaction auxiliary.

The amino-(thio)phenol derivatives of the general formula (VI) are obtained, for example, when nitro-(thio)phenol derivatives of the general formula (VIII)

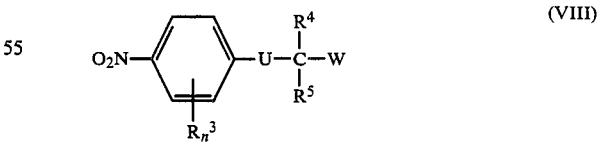

in which $R^3$, $R^4$, U, W and n have the meanings given above, are hydrogentated with Raney nickel in the presence of a diluent at pressures of 60 to 90 bar and at temperatures between 20° and 100° C.

The nitro-(thio)phenol derivative of the general formula (VIII) are known and can be obtained by known processes, for example by reacting 4-halogenonitrobenzenes of the general gormula (IX)

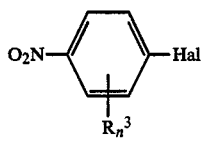 (IX)

in which
R³ and n have the meanings given above and
Hal represents halogen,
with (thio)alcohols of the general formula (X)

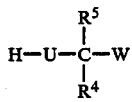 (X)

in which
R⁴, R⁵, U and W have the meanings given above, in the presence of a diluent, such as, for example, dimethyl sulphoxide, N-methylpyrrolidone or sulpholane and in the presence of an acid-binding agent, such as, for example, sodium hydride, sodium hydroxide and potassium hydroxide or sodium alcoholate or potassium alcoholate, at temperatures between $+20°$ and $+200°$ C.

The 4-halogenonitrobenzenes of the general formula (IX) and the (thio)alcohols of the general formula (X) are know compounds or can be produced by known methods.

The phenol derivatives of the general formula (XI)

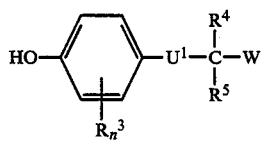 (XI)

in which
R³, R⁴, R⁵, W and n have the meanings given above and
U¹ represents oxygen,
are in some cases known or can be prepared in a simple manner by known processes, when phenol derivatives of the general formula (XII)

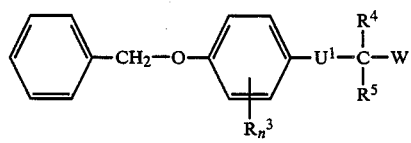 (XII)

in which
R³, R⁴, R⁵, W and n have the meanings give above and
U¹ represents oxygen,
are hydrogenated with Pd/C or PtO₂ in the presence of a diluent at pressures of 1 to 90 bar and at temperatures between 20° C. and 100° C.

The phenol derivatives of the general formula (XIII)

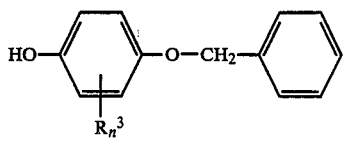 (XIII)

in which R³ and n have the meanings given above, are reacted with compounds of the general formula (V)

$$L-V-W \quad (V)$$

in which
V and W have the meanings given above and
L represents halogen, alkylsulphonate or arylsulphonate,
in the presence of a diluent such as, for example, dimethyl sulphoxide, N-methylpyrrolidone or sulpholane and in the presence of an acid-binding agent, such as, for example, sodium hydride, sodium hydroxide and potassium hydroxide or sodium alcoholate and potassium alcoholate at temperatures between 20° C. and 200° C.

A general definition of the thiazole derivatives furthermore required as starting substances for carrying out the process (A) according to the invention is given by the formula (III). In this general formula (III), the radicals R¹ and R² preferably represent those radicals which have already been mentioned as preferred for these substituents in the description of the substances of the general formula (I) according to the invention. Hal preferably represents fluorine, chlorine and bromine.

By way of example, the following thiazolyl derivatives of the general formula (III) may be mentioned: 4-methyl-2-chlorothiazole, 5-methyl-2-chlorothiazole, 4,5-dimethyl-2-chlorothiazole, 4-ethyl-5-methyl-2-chlorothiazole, 5-methyl-5-ethyl-2-chlorothiazole and 4,5-diethyl-2-chlorothiazole.

The thiazole derivatives of the general formula (III) are known or can, in principle, be obtained by simple processes. Ref. G. Vernin V. J. Metzger, Bull. Soc. Chim. France 2498 (1963).

A definition of the thiazolyl-(thio)phenols required as starting substances for carrying out the process (B) according to the invention is given by the general formula (IV). In the general formula (IV), R¹, R², R³, X and n preferably or particularly preferably represent those radicals which have radicals which have already been mentioned in the description of the substances of the formula (I) according to the invention as being preferred or particularly preferred for the substituents, and U¹ represents oxygen.

The compounds of the general formula (IV)

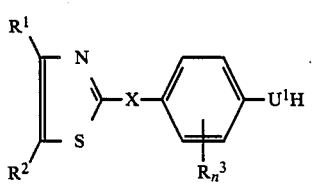 (IV)

in which
R¹, R², R³, X and n have the meanings given above and
U¹ represents oxygen,
are new and are also the subject of the present invention.

As examples of thiazolyl-(thio)phenols of the general formula (IV), there may be mentioned: 4-(4-methyl-2-thiazolyloxy)-phenol, 4-(4-methyl-2-thiazolylthio)-phenol, 4-(5-methyl-2-thiazolyloxy)-phenol, 4-(5-methyl-2-thiazolylthio)-phenol, 4-(4,5-dimethyl-2-thiazolyloxy)-phenol, 4-(4,5-dimethyl-2-thiazolylthio)-phenol, 4-(4-ethyl-5-methyl-2-thiazolyloxy)-phenol, 4-(4-ethyl-5-methyl-2-thiazolylthio)-phenol, 4-(4-methyl-5-ethyl-2-thiazolyloxy)-phenol, 4-(4-methyl-5-ethyl-2-thiazolylthio)-phenol, 4-(4,5-diethyl-2-thiazolyloxy)-phenol and 4-(4,5-diethyl-2-thiazolylthio)-phenol.

Thus, thiazolyl-(thio)phenols of the general formula (IV) are obtained when (C) 2-halogenothiazole derivatives of the general formula (III)

in which
$R^1$ and $R^2$ have the meanings give above and
Hal represents halogen, in particular fluorine, chlorine and bromine,
are reacted with compounds of the general formula (XIV)

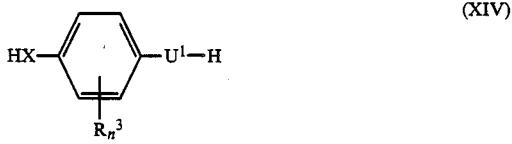

in which $R^3$, $U^1$, X and n have the meanings given above, in the presence of a solvent and in the presence of an acid-binding agent.

A general definition of the 2-halogenothiazoles required in the above process (C) as starting substances is given by the formula (III).

In this formula, $R^1$ and $R^2$ preferably have those meanings which have already been mentioned in connection with the description of the substances of the general formula (I) according to the invention. Hal preferably represent fluorine, chlorine or bromine. The compounds of the general formula (III) are known and may be prepared in a simple manner (G. Vernin v. J. Metzger, Bull. Chim. Soc. France 2498 (1963)).

A general definition of the educts required in addition in the process (C) is given by the formula (XIV). In this formula, $R^3$, $U^1$, X and n preferably have those meanings which already been mentioned as preferable for the radicals or this index in connection with the description of the substances of the general formula (IV) according to the invention.

The compounds of the general formula (XIV) are known or can, in principle, be obtained in a simple manner by known processes.

All acid acceptors usually utilizable for reactions of this type can be used as acid-binding agents in carrying out process (C), preferably alkali metal and alkaline earth metal oxides, hydroxides and carbonates, and in addition alkali metal alcoholates, amides and hydrides.

All customary inert organic solvents can be used as diluents in carrying out process (C). Preferably, ethers, such as dioxane, tetrahydrofuran, glycol dimethyl ether, as well as nitriles, for example acetonitrile and also strongly polar solvents, such as dimethylformamide, dimethyl sulphoxide, sulpholane and N-methylpyrrolidone, may be used.

The reaction temperatures can be varied within a relatively large temperature range in carrying out the process (C) and in general lie between 0° C. and 220° C., preferably 50° C. and 180° C.

The reaction according to process (C) is generally performed at normal pressure.

In carrying out process (C), the starting substances of the general formulae (III) and (XIV) are generally reacted in approximately equimolar amounts. It is also possible, however, to use one or other of the components in a relatively large excess. Working up is carried out by the usual processes.

A general definition of the compounds additionally required as starting substances in process (B) is given by the formula (V)

$$L-V-W \qquad (V)$$

In this formula, V and W preferably have those meanings which have already been mentioned as preferred for the substituents in the description of the substances of the general formula (I) according to the invention. L preferably represents chlorine, bromine, iodine, methylsulphonyl, ethylsulphonyl, phenylsulphonate, tosylate or mesylate.

By way of example, the following compounds of the general formula (V) may be mentioned: isobutyl tosylate, neopentyl tosylate, 2,2-dimethyl-1-butyl tosylate, 2,2-dimethyl-1-pentyl tosylate, 2,2-dimethyl-3-methoxy-1-propyl tosylate, 2,2-dimethyl-3-ethoxy-1-propyl tosylate, 2-methyl-2-methoxy-1-propyl tosylate, 2,2-dimethyl-3-fluoro-1-propyl tosylate, 2,2-dimethyl-3-chloro-1-propyl tosylate, 2,2-di-(chloromethyl)-1-propyl tosylate, 2,2-di(chloromethyl)-3-chloro-1-propyl tosylate, 2,2-dimethyl-4-nitrilo-1-butyl tosylate, 3,3-dimethyl-2-hydroxy-1-butyl tosylate, solketal tosylate, 2-ethoxycarbonyl-2-methyl-1-propyl tosylate, hydroxypivalaldehyde tosylate, 1-chloropinacolin, prenyl bromide, methallyl chloride, 2-fluoromethyl-allyl chloride, trifluoroethylphenyl sulphonate, 3-methyl-3-tosyloxymethyl-oxetane, 3-ethyl-3-mesyloxyethyl-oxetane, 3-isopropyl-3-tosyloxymethyl-oxetane, 2-methyl-2-tosyloxymethyl-pyran, chloromethyltrimethylsilane and 3,3-dimethyl-1-butyl-mesylate.

The compounds of the general formula (V) are in some cases known and can, in principle, be obtained in a simple manner by known methods (see, for example, A,. Coortin, H. R. von Tobel, G. Auerbach Helv. Chim. Acta 63, 1412 (1980)).

All inert solvents can be employed as diluents in the process (A) according to the invention. Those which may preferably be used are halogenohydrocarbons, such as methylene chloride, chloroform, tetrachloromethane, chlorobenzene and o-dichlorobenzene, and hydrocarbons such as toluene, xylene and tetralin, and also cyclic ethers, such as tetrahydrofuran and dioxane, and furthermore carboxylic acid esters, such as ethyl acetate and glycol monomethyl ether acetate and also strongly polar solvents, such as dimethyl sulphoxide, sulpholane, N-methylpyrrolidone, dimethylacetamide and dimethylformamide.

All customary acid acceptors are suitable as acid-binding agents for the reaction as described in process (A) according the invention. Tertiary amines, such as triethylamine, pyridine and N,N-dimethylaniline, and also alkaline earth metal oxides, such as magnesium oxide and calcium oxide, and also alkali metal and alkaline earth metal carbonates, such as sodium carbonate, potassium carbonate and calcium carbonate and also alkali metal and alkaline earth metal hydroxides, such as lithium hydroxide, sodium hydroxide, potassium hydroxide and calcium hydroxide, alkali metal and alkaline earth metal alcoholates such as sodium ethylate, sodium ethylate, potassium tert.-butylate and magnesium ethylate, alkali metal and alkaline earth metal hydrides such as sodium hydride, potassium hydride and calcium hydride may preferably be used.

The reaction temperatures can be varied within a relatively large range in carrying out the process (A) according to the invention. In general, temperatures between $-20°$ C. and $+200°$ C., preferably between $50°$ C. and $160°$ C., are used.

In carrying out the process (A) according to the invention, the starting substances of the formulae (II) and (III) and optionally also the base are generally used in approximately equivalent amounts. It is also possible, however, to employ one or other of the reaction components in a relatively large excess. Working up is carried out by the usual methods.

Those diluents and acid-binding agents which are also suitable for process (A) can preferably be used as diluents and acid-binding agents in the process (B) according to the invention.

The reaction temperatures can also be varied within a relatively large range in process (B) according to the invention. In general, temperatures between $-20°$ C. and $+250°$ C., preferably between $50°$ C. and $180°$ C., are used.

In carrying out process (B) according to the invention, the starting substances of the general formulae (IV) and (V) and optionally also the base are generally used in approximately equimolar amounts. It is also possible, however, to employ one or other of the reaction components in a relatively large excess.

The active compounds according to the invention can be used as defoliants, desiccants, agents for destroying board-leaved plants and, especially, as weedkillers. By weeds, in the broadest sense, there are to be understood all plants which grow in locations where they are undesired. Whether the subtances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopercurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

The active compounds according to the invention of the general formula (I) can be used with particularly good success for selectively combating monocotyledon and dicotyledon weeds, in particular in monocotyledon cultures, such as wheat in the post-emergence process.

When used in the post-emergence process, the active compounds according to the invention can be applied alone or in combination with emulsifiable oils, surface-active substances and other additives.

The active compounds according to the invention moreover engage in the metabolism of the plants and can therefore be employed as growth regulators.

Experience to date of the mode of action of plant growth regulators has shown that an active compound can also exert several different actions on plants. The actions of the compounds depend essentially on the point in time at which they are used, relative to the stage of development of the plant, and on the amounts of active compound applied to the plants or their environment and the way in which the compounds are applied. In every case, growth regulators are intended to influence the crop plants in the particular manner desired.

The amount of leaves on plants can be controlled, under the influence of growth regulators, so that defoliation of the plants at a desired point in time is achieved. Such defoliation is of great importance in the mechanical harvesting of cotton, but is also of interest for facilitating harvesting in other crops, such as, for example, in viticulture. Defoliation of the plants can also be carried out to lower the transpiration of plants before they are transplanted.

The active compounds can be converted to the customary formulations, such as solutions, emulsions, wettable powders, suspensions, powders, dusting agents, pastes, soluble powders, granules, suspension emulsion concentrates, natural and synthetic materials impregnated with active compound and very fine capsules in polymeric substances.

These formulations are produced in known manner, for example by mixing the active compounds with extenders, that is, liquid solvents, and/or solid carriers, optionally with the use of surface-active agents, that is, emulsifying agents and/or dispersing agents, and/or foam-forming agents.

In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly-disperse silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkylsulphonates, alkyl sulphates, aryl sulphonates as well as albumin hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids can be used in the formulations. Further additives may be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

When used as herbicides, the active compounds according to the invention, as such or in the form of their formulations, can also be used, for combating weeds, as mixtures with known herbicides, finished formulations or tank mixes being possible.

Suitable herbicides for the mixtures are known herbicides, such as, for example, 1-amino-6-ethylthio-3-(2,2-dimethylpropyl)-1,3,5-triazine-2,4(1H,3H)-dione or N-(2-benzothiazolyl)-N,N'-dimethylurea for combating weeds in cereals; 4-amino-3-methyl-6-phenyl-1,2,4-triazin-5(4H)-one for combating weeds in sugar beets, and 4-amino-6-(1,1-dimethylethyl)-3-methylthio-1,2,4-triazin-5(4H)-one for combating weeds in soy beans. Suitable compounds for admixture include the following:

Ureas (for example methabenzothiazuron, chlorotuluron, isoproturon), sulphonylureas (for example chlorosufuron), triazines (for example atrazine), terbutryne, cyanazine), triazinones (for example ethiozine, metribuzine), triazindiones (for example amethydiones), diphenyl esters (for example bifenox), benzonitriles (for example ioxynil, bromoxynil), phenoxyalkanecarboxylic acids (for example 2,4 D, 2,4 DP, MCPA, MCPP etc.), aryloxy or heteroaryloxyphenoxypropionic acids (for example illoxan, whip, (trimethylsilyl)methyl (R)-2-[4-(3,5-dichloropyridyl-2-oxy)-phenoxy]-propionate, imidazolinones (for example imazamethabenz), bentazones and pyridates.

Some mixtures surprisingly also exhibit a synergistic effect.

Mixtures with other known active compounds, such as fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants.

They can also be incorporated into the soil before sowing.

The amount of active compound used can vary within a relatively large range. It depends essentially on the nature of the desired effect. In general, the amounts used are between 0.01 and 10 kg of active compound per hectare of soil surface, preferably between 0.05 and 5 kg per ha.

PREPARATION EXAMPLES

Example 1

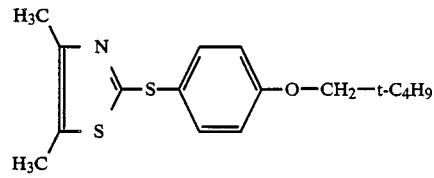

(Process A)

1.1 g (0.045 mol) of 80% sodium hydride are added at room temperature to 6.12 g (0.034 mol) of 4-neopentyloxythiophenol in 75 ml of absolute dimethylformamide. After stirring for ten minutes at room temperature, 5 g (0.034 mol) of 2-chloro-4,5-dimethylthiazole are added and the mixture is heated at reflux for 6 hours. The solvent is then distilled off and the reaction mixture is added to 500 ml of water. After filtering off with suction and drying, 10 g of the desired thiazole (96% of theory) are obtained, melting point: 82° C.

Example 2

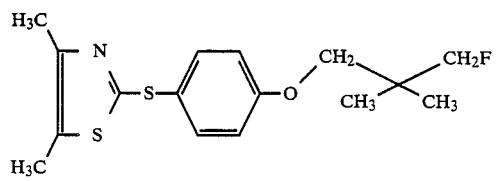

(Process B)

4.74 g (20 mmol) of 4-(4,5-dimethyl-2-thiazolylthio)-phenol in 20 ml of N-methylpyrrolidone are treated under a nitrogen atmosphere with 2.69 g (24 mmol) of potassium tert.-butylate and the mixture is stirred for 5 minutes. After the addition of 4.05 g (22 mmol) of 3-fluoroneopentyl tosylate, it is heated to 150° C. for 6 hours. The reaction mixture is stirred into 150 ml of 1N NaOH and extracted 3 times with toluene, and the extract is dried with MgSO$_4$ and concentrated on a rotary evaporator using a waterpump vacuum. The residue is chromatographed on silica gel with cyclohexane/ethyl acetate 3:1. By crystallization from ethyl acetate/n-hexane, 3.68 g (56.6%) of the thiazolyl ether are obtained, with a melting point of 85° C.

The compounds of the general formula (I) listed in the tables according to structure can be prepared according to the methods given in the preceding examples and in the description.

EXAMPLE 17

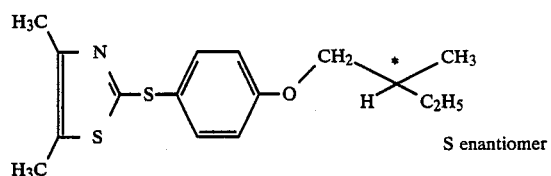

S enantiomer $^1$H—NMR (200 MHz, CDCl$_3$) δ=0.95 (t; 3H, CH$_2$CH$_3$), 1.03 (d; 3H, *CH—CH$_3$), 1.29 (m; 1H, CH$_2$CH$_3$), 1.55 (m; 1H, *CH<1.78 (m; 1H, CH$_2$CH$_3$), 2.21 2.27 (2s; 6H, thiazolyl-4-CH$_3$ and 5—CH$_3$), 3.79 (ABq; 2H, O—CH$_2$—*CH), 6.92 7.54 (AA'BB'; 4H, Ar—H).

TABLE 2

| Ex. No. | R$^1$ | R$^2$ | R$^3$ | n | X | U | R$^4$ | R$^5$ | R$^9$ | R$^{10}$ | R$^{11}$ | melting point (°C.) |
|---|---|---|---|---|---|---|---|---|---|---|---|---|
| 30 | CH$_3$ | CH$_3$ | H | O | S | O | H | H | H | H | CH$_3$ | 31 |
| 31 | CH$_3$ | CH$_3$ | H | O | S | O | H | H | H | H | CH$_2$F | Oil |

TABLE 3

| Ex. No. | R$^1$ R$^2$ | R$^3$ | n | X | U | R$^4$ | R$^5$ | E | R$^{12}$ | Melting point (°C.) |
|---|---|---|---|---|---|---|---|---|---|---|
| 32 | CH$_3$ CH$_3$ | H | | O | S | O | H | H | O | CH$_3$ | 47 |
| 33 | CH$_3$ CH$_3$ | H | | O | S | O | H | H | O | —C(CH$_3$)$_3$ | 109 |

Compounds

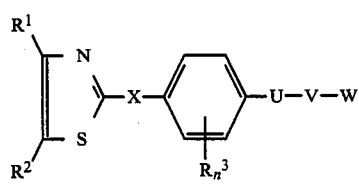

(I)

TABLE 1

| Ex. No. | R$^1$ | R$^2$ | R$^3$ | n | X | U | D | R$^4$ | R$^5$ | R$^6$ | R$^7$ | R$^8$ | melting point °C. |
|---|---|---|---|---|---|---|---|---|---|---|---|---|---|
| 3 | CH$_3$ | CH$_3$ | H | — | O | O | C | H | H | CH$_3$ | CH$_3$ | CH$_3$ | n$_D^{20}$: 1.5321 |
| 4 | CH$_3$ | CH$_3$ | H | — | S | O | C | H | H | H | CH$_3$ | CH$_3$ | 34 |
| 5 | CH$_3$ | CH$_3$ | H | — | S | O | C | H | H | H | CH$_3$ | C$_2$H$_5$ | Oil |
| 6 | CH$_3$ | CH$_3$ | H | — | S | O | C | H | H | CH$_3$ | CH$_3$ | C$_2$H$_5$ | 31 |
| 7 | CH$_3$ | CH$_3$ | H | — | S | O | C | H | H | CH$_3$ | CH$_3$ | C$_3$H$_7$ | Oil |
| 8 | CH$_3$ | CH$_3$ | H | — | S | O | C | H | H | CH$_3$ | CH$_3$ | CH$_2$Cl | 44 |
| 9 | CH$_3$ | CH$_3$ | H | — | S | O | C | H | H | CH$_3$ | CH$_3$ | CH$_2$OCH$_3$ | Oil |
| 10 | CH$_3$ | CH$_3$ | H | — | S | O | C | H | H | CH$_3$ | CH$_3$ | CH$_2$OC$_2$H$_5$ | 22 |
| 11 | CH$_3$ | CH$_3$ | H | — | S | O | C | H | H | CH$_3$ | —CH$_2$—O—CH$_2$— | | 74 |
| 12 | CH$_3$ | CH$_3$ | H | — | S | O | C | H | H | C$_2$H$_5$ | —CH$_2$—O—CH$_2$— | | 35 |
| 13 | CH$_3$ | CH$_3$ | H | — | S | O | C | H | H | CH$_3$ | CH$_3$ | OCH$_3$ | 30 |
| 14 | CH$_3$ | CH$_3$ | H | — | S | O | C | H | H | CH$_3$ | —O—(CH$_2$)$_4$— | | 53 |
| 15 | CH$_3$ | CH$_3$ | H | — | S | O | C | H | H | F | F | F | 41 |
| 16 | CH$_3$ | CH$_3$ | H | — | S | S | C | H | H | CH$_3$ | CH$_3$ | CH$_3$ | 40 |
| 18 | CH$_3$ | CH$_3$ | H | O | S | O | C | H | H | H | CH$_3$ | C$_3$H$_7$ | Oil |
| 19 | CH$_3$ | CH$_3$ | H | O | S | O | C | H | H | H | C$_2$H$_5$ | C$_4$H$_9$ | Oil |
| 20 | CH$_3$ | CH$_3$ | H | O | S | O | C | H | H | H | H | C(CH$_3$)$_3$ | Oil |
| 21 | CH$_3$ | CH$_3$ | H | O | S | O | C | H | H | H | H | C(CH$_3$)$_2$OCH$_3$ | Oil |
| 22 | CH$_3$ | CH$_3$ | H | O | S | O | C | H | H | H | —O—(CH$_2$)$_4$— | | 58 |
| 23 | CH$_3$ | CH$_3$ | H | O | S | O | C | H | H | CH$_3$ | —O—CH=CH—(CH$_2$)$_2$— | | 61 |
| 24 | CH$_3$ | CH$_3$ | H | O | S | O | C | H | H | CH$_3$ | —CH$_2$—OC(CH$_3$)$_2$—O—CH$_2$— | | 76 |
| 25 | CH$_3$ | CH$_3$ | H | O | S | O | C | H | H | CH$_3$ | —O—(CH$_2$)$_3$—O— | | Oil |
| 26 | CH$_3$ | CH$_3$ | H | O | S | O | C | H | H | CH$_3$ | —O—CH$_2$—C(CH$_3$)$_2$—CH$_2$—O— | | 67 |
| 27 | CH$_3$ | CH$_3$ | H | O | S | O | C | H | H | CH$_3$ | —O—CH(CH$_3$)—CH$_2$—C(CH$_3$)$_2$—O— | | Oil |
| 28 | CH$_3$ | CH$_3$ | H | O | S | O | C | H | CH$_3$ | CH$_3$ | CH$_3$ | CH$_3$ | 46 |
| 29 | CH$_3$ | CH$_3$ | 3-Cl | 1 | S | O | C | H | H | CH$_3$ | CH$_3$ | CH$_3$ | 52 |

TABLE 3-continued

| Ex. No. | | Melting point (°C.) |
|---|---|---|
| 34 | (structure) | 41 |
| 35 | (structure) | 76 |
| 36 | (structure) | 69 |

PREPARATION OF THE STARTING PRODUCTS

Example (a)

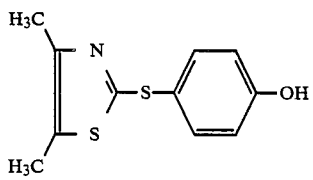

(Process C)

40 g (0.61 mol) of powdered, ca. 85% KOH are initially taken in 366 ml of N-methylpyrrolidone under a nitrogen atmosphere. 71 g (0.61 mol) of 4-mercaptophenol are added dropwise at 60° C. 90 g (0.61 mol) of 4,5-dimethyl-2-chlorothiazole are then added dropwise at 100° C. and stirred for a further 2 hours at 100° C. About ⅔ of the N-methylpyrrolidone is then distilled off under a high vacuum, the residue is poured into water and the solution is adjusted to pH 7. It is then extracted with chloroform, dried and concentrated in the water-pump vacuum on a rotary evaporator. After recrystallization from methanol, 103 g (75% of theory) of 4,5-dimethylthiazolylthio)-phenol of melting point 145° C. are obtained.

USE EXAMPLE

Example A

Post-Emergence Test

Solvent: 5 parts by weight of acetone
Emulsifier: 1 part by weight of alkylaryl polyglycol ether To produce a suitable preparation of active compound, 1 part by weight of active compound is mixed with the state amount of solvent, the stated amount of emulsifier is added and the concentrate is diluted with water to the desired concentration.

Test plants 5 to 15 cm high are sprayed with the preparation of the active compound in such a way that the amounts of active compound desired in each case are applied per unit area. The concentration of the spray is chosen such that the amounts of active compound desired in each case are applied in 2000 liters water/ha. After three weeks, the degree of damage to the plants is rated in % damage in comparison to the development of the untreated control. The figures denote:

0%=no action (like untreated control)
100%=total destruction

In this test the compounds according to the preparation Examples 1,8,9 and 13, for example, show a very good selective herbicidal activity against weeds, such as, for example, Abutilon, Datura or Stellaria.

It will be understood that the specification and examples are illustrative but not limitative of the present invention and that other embodiments within the spirit and scope of the invention will suggest themselves to those skilled in the art.

We claim:

1. A thiazolyl derivative of the formula

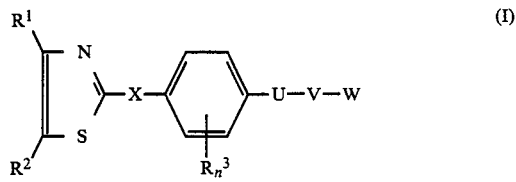

in which
R$^1$ represents hydrogen or C$_1$-C$_4$-alkyl,
R$^2$ represents hydrogen C$_1$-C$_4$-alkyl,
with the proviso that R$^1$ and R$^2$ do not simultaneously represent hydrogen,
X represents oxygen or sulphur,
R$^3$ represents hydrogen, halogen, nitro, amino, cyano, C$_1$-C$_4$-alkyl, C$_1$-C$_4$-halogenoalkyl, C$_1$-C$_4$-alkoxy, C$_1$-C$_4$-halogenoalkoxy, wherein the radicals R$^3$ can be identical or different,
n represents a number from 1-4,
U represents oxygen or sulphur,
V represents a

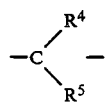

group,
R$^4$ and R$^5$ independently of one another represent hydrogen, C$_1$-C$_4$-alkyl, C$_1$-C$_4$-alkoxy-C$_1$-C$_4$-alkyl or C$_1$-C$_4$-halogenoallyl, W represents a radical

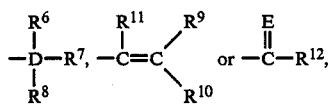

D represents carbon or silicon,
E represents oxygen or sulphur,
$R^6$, $R^{11}$ and $R^{12}$ independently of one another represent hydrogen, halogen, $C_1-C_6$-alkyl or $C_1-C_6$-halogenoalkyl, $R^7$ represents hydrogen, halogen, or $C_1-C_4$-alkyl which is optionally substituted by halogen; or represents $C_1-C_6$-alkoxy, $C_1-C_6$-alkoxy-$C_1-C_6$-alkyl, or $C_1-C_6$-alkylthio, $R^8$ represents halogen, a saturated or unsaturated aliphatic radical with 1 to 6 carbon atoms which is optionally substituted by halogen; or represents $C_1-C_6$-alkoxy, $C_1-C_6$-alkoxy-$C_1-C_6$-alkyl, $C_1-C_6$-alkylthio, formyl, $C_1-C_6$-alkylcarbonyl, $C_1-C_6$-alkoxycarbonyl, open-chain or cyclic acetal, open-chain or cyclic thioacetal, or $R^7$ and $R^8$, together with the carbon atom to which they are bonded, form a 3- to 8-membered ring, which, apart from carbon, can also contain oxygen and/or sulphur and/or nitrogen as ring members and which can optionally be substituted by halogen, $C_1-C_4$-alkyl, $C_1-C_4$-alkoxy or $C_1-C_4$-alkoxy-$C_1-C_4$-alkyl and which can contain one or more double bonds, or $R^6$, $R^7$ and $R^8$, together with the carbon atom to which they are bonded, represent a radical of the structure

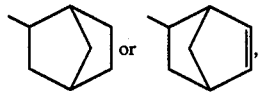

and
$R^9$ and $R^{10}$ independently of one another represent hydrogen, halogen, $C_1-C_6$-alkyl or $C_1-C_6$-halogenoalkyl.

2. A compound according to claim 1, in which
$R^3$ represents hydrogen, halogen, $C_1-C_4$-alkyl, $C_1-C_4$-halogenoalkyl, $C_1-C_4$-alkoxy or halogeno-$C_1-C_4$-alkoxy, wherein the radicals $R^3$ can be identical or different, $R^8$ represents halogen, $C_1-C_6$-alkyl, $C_1-C_6$-alkoxy, $C_1-C_6$-alkoxy-$C_1-C_6$-alkyl, $C_1-C_6$-alkylthio, formyl, $C_1-C_6$-alkylcarbonyl, $C_1-C_6$-alkoxycarbonyl, $C_2-C_6$-alkenyl, $C_2-C_6$-alkinyl, halogeno-$C_1-C_6$-alkyl, halogeno-$C_2-C_6$-alkenyl, open-chain acetal, cyclic acetal with 5 or 6 ring members, open-chain thioacetal or cyclic thioacetal with 5 or 6 ring members, or $R^7$ and $R^8$, together with the carbon atom to which they are bonded, form a 5- or 6-membered ring which, part from carbon, can also contain 1 or 2 oxygen and/or sulphur and/or nitrogen atoms as ring members and which can be substituted by fluorine, chlorine, bromine and iodine, $C_1-C_4$-alkyl, $C_1-C_4$-alkoxy and/or $C_1-C_4$-alkoxy-$C_1-C_4$-alkyl and which can contain one or two double bonds or $R^6$, $R^7$ and $R^8$, together with the carbon atoms to which they are bonded, represent a radical of the structure

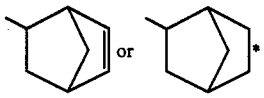

3. A compound according to claim 1, in which
$R^1$ represents hydrogen, methyl or ethyl,
$R^2$ represents hydrogen, methyl or ethyl, with the proviso that $R^1$ and $R^2$ do not simultaneously represent hydrogen, $R^3$ represents hydrogen, halogen, methyl, ethyl methoxy, ethoxy, halogeno-$C_1-C_2$-alkyl or halogeno-$C_1-C_2$-alkoxy, wherein the radicals $R^3$ can be identical or different, $R^4$ and $R^5$ independently of one another in each case represent hydrogen, methyl, ethyl, methoxymethyl, methoxyethyl, ethoxymethyl, ethoxyethyl or halogeno-$C_1-C_2$-alkyl, $R^6$, $R^{11}$ and $R^{12}$ independently of one another represent hydrogen, fluorine, chlorine, bromine, iodine, $C_1-C_4$-alkyl or halogeno-$C_1-C_4$-alkyl, $R^7$ represents hydrogen, fluorine, chlorine, bromine, iodine, $C_1-C_4$-alkyl, $C_1-C_4$-alkoxy, $C_1-C_4$-alkoxy-$C_1-C_4$-alkyl, $C_1-C_4$-alkylthio or halogeno-$C_1-C_4$-alkyl, $R^8$ represents fluorine, chlorine, bromine, iodine, $C_1-C_4$-alkyl, $C_1-C_4$-alkoxy, $C_1-C_4$-alkoxy-$C_1-C_4$-alkyl, $C_1-C_4$-alkylthio, formyl, $C_1-C_4$-alkylcarbonyl, $C_1-C_4$-alkoxycarbonyl, $C_2-C_4$-alkenyl, $C_2-C_4$-alkinyl, halogeno-$C_1-C_4$-alkyl, halogeno-$C_2-C_4$-alkenyl, open-chain acetal, cyclic acetal with 5 or 6 ring members, open-chain thioacetal or cyclic thioacetal with 5 or 6 ring members, or $R^7$ and $R^8$, together with the carbon atom to which they are bonded, form a 5- or 6-membered ring which, apart from carbon, can also contain 1 or 2 oxygen and/or sulphur and/or nitrogen atoms as ring members and which can be substituted by fluorine, chlorine, bromine and iodine, methyl, ethyl, methoxy, ethoxy, methoxymethyl, methoxyethyl, ethoxymethyl or ethoxyethyl and which can contain one or two double bonds, or $R^6$, $R^7$ and $R^8$, together with the carbon atom to which they are bonded, represent a radical of the structure

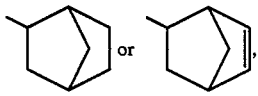

$R^9$ and $R^{10}$ independently of one another represent hydrogen, halogen, $C_1-C_2$-alkyl or halogeno-$C_1-C_2$-alkyl.

4. A compound according to claim 1, wherein such compound is 4,5-dimethyl-2-(4-neopentyloxyphenylthio)-thiazole of the formula

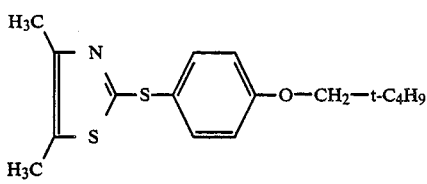

5. A compound according to claim 1, wherein such compound is 4,5-dimethyl-2-(4-chloroneopentyloxyphenylthio)-thiazole of the formula

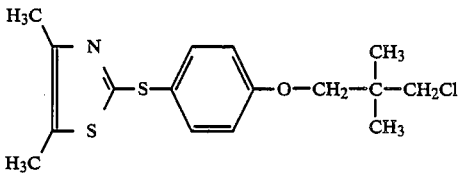

6. A compound according to claim, wherein such compound is 4,5-dimethyl-2-(4-methoxyneopentyloxyphenylthio)-thiazole

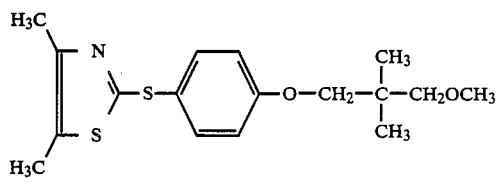

7. A compound according to claim 1, wherein such compound is 4,5-dimethyl-2-(4-[2-methoxy-2-methylpropyloxy]phenylthio)-thiazole of the formula

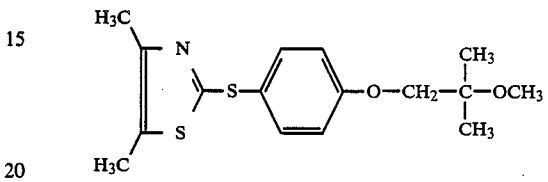

8. A herbicidal composition comprising a herbicidally effective amount of a compound according to claim 1 and a diluent.

9. A method of combating unwanted vegetation which comprises applying to such vegetation or to a locus from which it is desired to exclude such vegetation a herbicidally effective amount of a compound according to claim 1.

10. The method according to claim 9, wherein such compound is
4,5-dimethyl-2-(4-neopentyloxyphenylthio)-thiazole,
4,5-dimethyl-2-(4-chloroneopentyloxyphenylthio)-thiazole,
4,5-dimethyl-2-(4-methoxyneopentyloxyphenylthio)-thiazole or
4,5-dimethyl-2-(4-[2-methoxy-2-methyl-propyloxy]-phenylthio)-thiazole.

* * * * *